United States Patent [19]

Brown

[11] 4,241,740

[45] Dec. 30, 1980

[54] BELLOWS TYPE INCENTIVE SPIROMETER

[76] Inventor: Joseph W. Brown, P.O. Box 385, Blue Springs, Mo. 64015

[21] Appl. No.: 17,591

[22] Filed: Mar. 5, 1979

[51] Int. Cl.³ .......................... A61B 5/08; B23P 11/02; F16J 3/04
[52] U.S. Cl. ..................................... 128/728; 29/454; 73/262; 92/42; 272/99
[58] Field of Search .............................. 128/727–730, 128/203.28, 204.28, 205.13–205.17; 272/99; 92/42; 417/472, 473; 73/262; 29/454; 84/376 R, DIG. 15

[56] References Cited

U.S. PATENT DOCUMENTS

| 51,002 | 11/1865 | Barnes .................................. 128/728 |
| 393,869 | 12/1888 | Warren ............................ 128/203.24 |
| 642,149 | 1/1900 | McKenzie ............................. 128/728 |
| 2,878,012 | 3/1959 | Crites ........................................ 92/42 |
| 3,086,515 | 4/1963 | Jones ..................................... 128/728 |
| 3,154,068 | 10/1964 | Reinert et al. ........................ 128/728 |
| 3,467,078 | 9/1969 | Bird et al. ............................. 128/728 |
| 3,530,566 | 9/1970 | McMurry et al. ................. 29/454 X |
| 3,559,639 | 2/1971 | Nagus et al. .......................... 128/728 |
| 3,635,214 | 1/1972 | Rand et al. ............................ 128/727 |
| 3,669,097 | 6/1972 | Fitz ...................................... 272/99 X |
| 3,821,950 | 7/1974 | Boehringer ............................ 128/728 |
| 3,849,864 | 11/1964 | Plummer ................................. 29/454 |
| 3,951,137 | 4/1976 | Conkle et al. .................... 128/730 X |

FOREIGN PATENT DOCUMENTS

| 2255070 | 5/1974 | Fed. Rep. of Germany .............. 92/42 |
| 595686 | 10/1925 | France ...................................... 128/728 |
| 744451 | 4/1933 | France ...................................... 128/728 |

*Primary Examiner*—Lee S. Cohen
*Attorney, Agent, or Firm*—Fishburn, Gold and Litman

[57] ABSTRACT

A spirometer comprises an upright, hollow frame structure having opposite end portions with an expansible and contractible bellows therein responsive to exhalation and inhalation. The bellows includes a hollow, resilient helical structure with a plurality of coils respectively having relatively broad upper and lower surfaces and relatively thin outer edges. Opposite end members close the helical structure, one of the closing end members being connected to one of the frame structure end portions for suspending the bellows inside the frame structure. A sheet of thin, fluid-impervious film extends the length of the helical structure when the helical structure is expanded and is heat shrunk onto the coils for forming convolutions engaging the upper and lower surfaces and outer edges. The sheath joins the opposite closed end members and defines an impervious outer wall structure for the bellows. A passage is connected to one of the closed end members and communicates with the bellows interior for transmitting inhalation and exhalation pressures thereto.

10 Claims, 5 Drawing Figures

U.S. Patent  Dec. 30, 1980  4,241,740
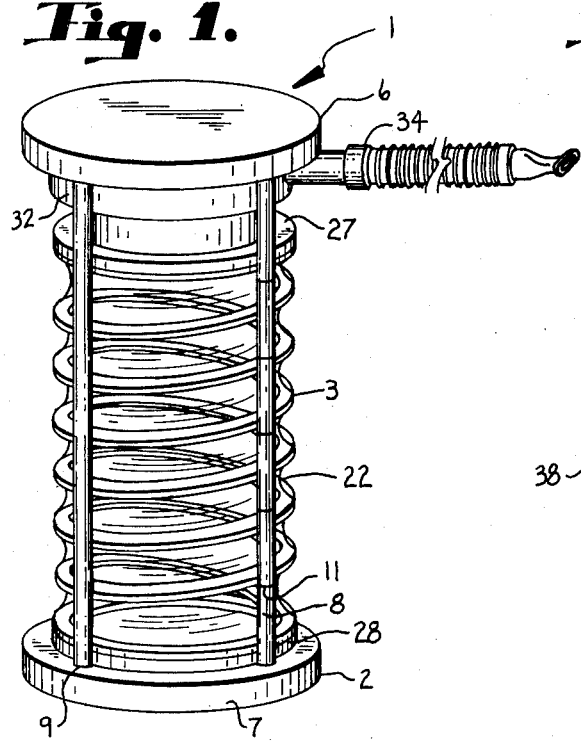
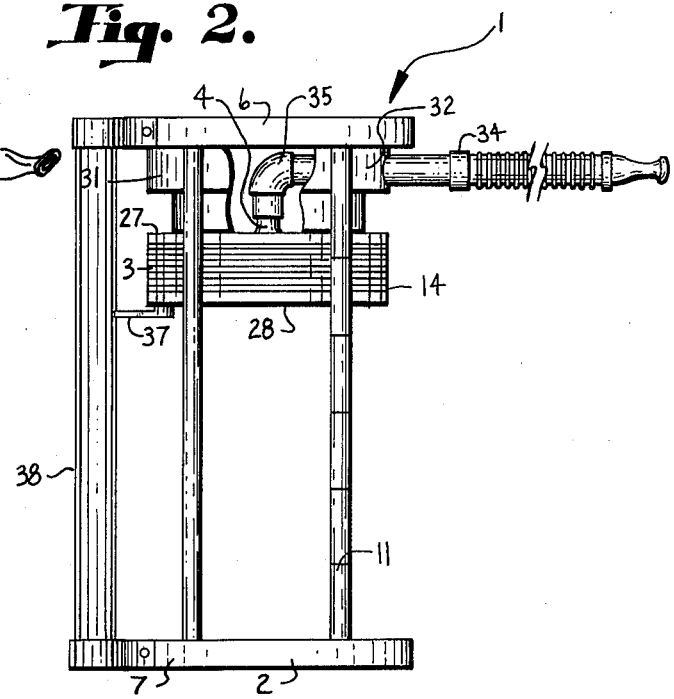
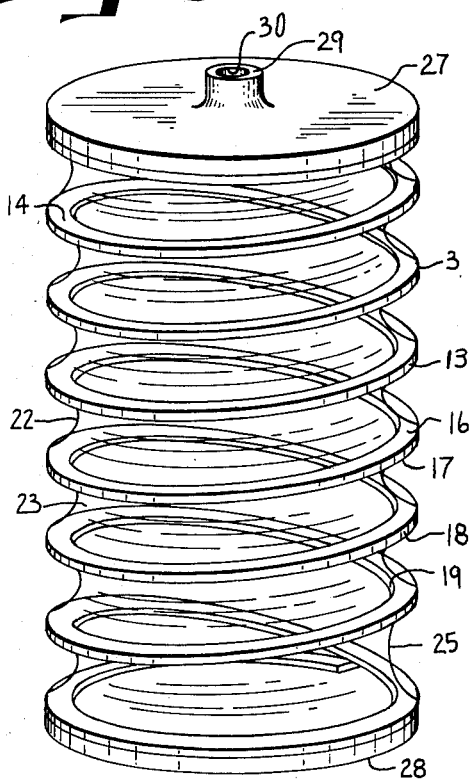
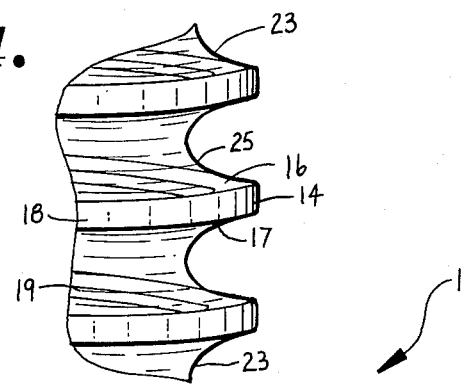
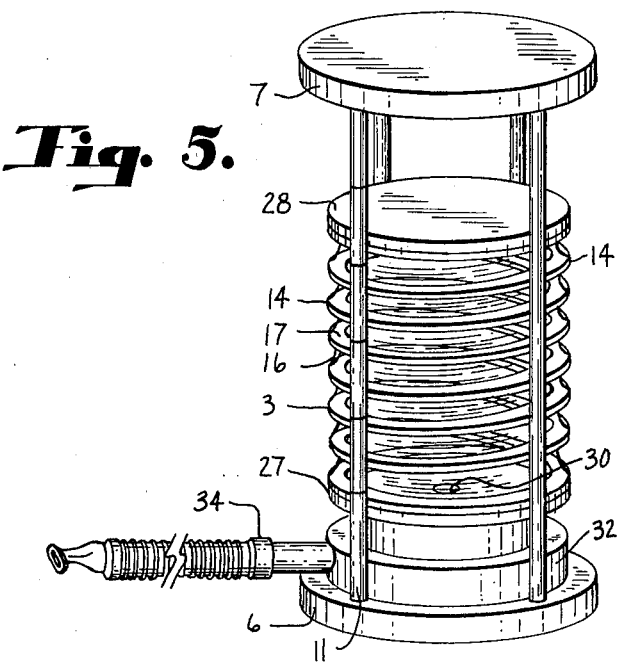

BELLOWS TYPE INCENTIVE SPIROMETER

This invention relates to a spirometer structure and particularly to a bellows and method of making same for a spirometer structure.

In the treatment of respiratory system disorders of patients with either restrictive or obstructive factors, deep breathing exercises with emphasis on sustained inspiration to total lung capacity or exhalation of full lung capacity has consistently been effective in inflating lung alveoli, excercising diaphram muscles and preventing pulmonary complications. These maneuvers have generally been accomplished under the guidance of physical therapists or by careful patient instruction emphasising the use of an incentive spirometer. Crucial to chest physical therapy, these excercises have been the mainstay of pulmonary prophylaxsis on many thoracic surgery services and have been effective in preventing atelectasis or collapse of alveoli, as determined by evaluation of control groups.

The patient needs to fully exercise the lungs and needs to both fully inhale and exhale which is often difficult to accomplish considering the physical state of the typical patient. Accordingly, a visual measuring means is desired which will provide volume indications to the patient during a prophylactic respiratory maneuver and so encourage self-motivated therapy.

Spirometer structures known in the art tend to be rather complex, expensive and imprecise devices which are relatively unresponsive to small pressure differentials. Further, bellows or pneumatic chambers useful in such spirometers all tend to be expensive, thereby increasing the cost to the patient and increasing the cost of medical care in general. Because the bellows structure is expensive, cleaning and sterilization after patient use is often attempted, however, such attempts are often unsatisfactorily accomplished because of the difficulty involved.

The principal objects of the present invention are: to provide a bellows or pneumatic chamber and a method of manufacturing same for a spirometer or other such structure which is inexpensive to produce and hence adapted for single patient use whereby the bellows is disposable; to provide an inhalation and exhalation spirometer apparatus for prophylatic respiratory maneuver; to provide such a spirometer structure including visual meter means indicating volumetric inhalation and exhalation ability; to provide a bellows or pneumatic chamber structure which is inexpensively produced and responsive to small pressure differentials; to provide such a bellows having an internal helical structure which can be manufactured to have a memory urging said helical structure toward either a contracted position or an expanded position; to provide a bellows structure manufactured of inexpensive materials; and to provide such a spirometer and bellows therefor which is relatively inexpensive, sturdy and efficient in use, and particularly well adapted for the intended purpose.

Other objects and advantages of this invention will become apparent from the following description taken in connection with the accompanying drawings wherein are set forth, by way of illustration and example, certain embodiments of this invention.

FIG. 1 is a perspective view of a spirometer structure embodying the present invention and showing an expanded bellows structure and patient breathing tube.

FIG. 2 is a elevational view of the spirometer structure and showing the bellows structure therefor in a contracted position.

FIG. 3 is an enlarged, perspective view of the bellows structure used in the spirometer structure.

FIG. 4 is a fragmentary, greatly enlarged view of portions of the bellows structure.

FIG. 5 is a perspective view of an inverted spirometer structure and showing the bellows structure and patient breathing tube therefor.

Referring to the drawings in more detail:

As required, detailed embodiments of the present invention are disclosed herein, however, it is to be understood that the disclosed embodiments are merely exemplary of the invention which may be embodied in various forms, therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally indicates a spirometer embodying the present invention and including an upright, hollow frame structure 2 having an expansible and contractible bellows 3 therein responsive to exhalation and inhalation pressures. A passage 4 communicates with an interior of the bellows 3 for transmitting inhalation and exhalation pressures from a patient to the bellows 3.

The exemplary frame structure 2 includes opposite end portions 6 and 7 in spaced vertical relation connected by a plurality of upright supports 8 positioned adjacent outer edges 9 of the end portions 6 and 7 and providing a hollow, cage-like structure for receipt of the bellows 3.

Additionally, a scale 11 is affixed to one of the upright supports 8 and visually indicates a volume of air within the portion of the bellows 3 positioned between scale markings.

Many suitable materials are available for use in the manufacture of the frame structure 2; however, to present a sanitary and sparkling appearance, it is preferred that the same be formed of a synthetic resin material, such as a plastic, which is relatively rigid and sufficiently sturdy for use and which may be readily fabricated. Moreover, it is preferred that the material used, though rigid, be slightly resilient so as not to shatter if dropped upon the floor.

The bellows 3, as best shown in FIG. 3, is comprised of a hollow, resilient, helical structure 13 with a plurality of coils 14 or single turns of the helical structure 13 respectively having relatively broad upper and lower surfaces 16 and 17 and relatively thin outer and inner edges 18 and 19. The helical structure 13 is of a thin, flat bar or strip wound with the thin edges defining the inner and outer diameters of the helical structure and when fully collapsed, the upper and lower surfaces 16 and 17 of adjacent coils or turns 14 are in contacting, overlying relation.

The helical structure 13 may be of any desired size with the flat bar or strip material of suitable size to provide a desired memory and expanding force. By way of example of suitable relative sizes is a helical structure 13 having a 3½ inch outside diameter with the flat bar of the coils 14 being 3/16 to ⅜ inches wide and 1/16 to ⅛ inches thick. The operating elongation relative to collapsed length ranges from 3 to 1 to 6 to 1 and requires an elongation force of 4 ounces. The helical structure 13 may be formed with a compressive memory so that it is normally collapsed and requires force for elongation or so that it is normally expanded and requires force for collapsing.

A sheath 22 of thin, fluid impervious film 23 extends the length of an expanded helical structure 13 and forms a plurality of convolutions 25 with contacting portions of the film 23 engaging the upper and lower surfaces 16 and 17 and the outer edge 18 of the coils 14, thereby maintaining a relative position of the film 23 on the helical structure 13. In the absence of a fixed relation between portions of the film 23 forming convolutions 25 and the respective coils or turns 14, the coils or turns 14 would tend to slip within the sheath 22 and thereby the bellows 3 would be less responsive to slight pressure differentials. Accordingly, the convolutions 25 fixed relative to the coils or turns 14 tend to reduce slippage and promote responsiveness. Preferably, the film 23 is of relatively lightweight plastic, such as polyethylene, of approximately 1 to 1½ mils in thickness and is heat shrinkable for purposes of manufacturing of the bellows 3 as described below.

The sheath 22 extends around the helical structure 13 in engagement therewith and defines an impervious outer wall structure for the bellows 3. Opposite closed end members 27 and 28 are fixed to opposite end coils or turns 14 of the helical structure 13, such as by adhesive or the like, for forming a closed pneumatic chamber.

In the illustrated example, FIG. 3, the passage 4 has a bore 30 through the end member 27 opening into the interior of the bellows 3 to communicate pressure differentials thereto. To mount the bellows 3 within the frame structure 2, a connector assembly 31 is affixed adjacent one of the frame structure end portions, such as the end portion 6 and includes, in the illustrated example, a cylindrical wall member 32 attached to an inside surface of the end portion 6 and having a breathing tube 34 extending therethrough with a elbow 35 on one end for connection to the passage 4.

Depending upon the weight of the end member 28 and the memory of the helical structure 13, the bellows 3 will be at rest, or in a balanced condition, for either inhalation or exhalation. In a structure such as shown in FIG. 2, the end member 28 preferably is of a weight slightly less than the elongation force to almost balance the resilient force for elongation or expansion. Where the bellows 3 is almost in a balanced condition and the weight of gravity tends to cause the bellows 3 to expand and fill with air to an extended position, such as shown in FIG. 1, the spirometer 1 can simply be inverted, such as shown in FIG. 5, to cause the weight of gravity to move the bellows 3 to a contracted position. Thus, a bellows 3 thereby affected by gravitational forces can be used either in an inhalational mode or an exhalational mode by inverting the spirometer 1. In such a structure shown in FIG. 5, the supports 8 act as guides maintaining the bellows 3 in a proper relationship for extension and prevent canting and binding. Moreover the upright supports may be variously situated and one or more may even extend upwardly through the bellows 3 with the proper seals therearound for comprising a center guide rod.

Additionally, recording means such as a stylus 37 on the end member 28 and a paper scroll 38 connected to the frame structure 2 records bellows movement during inhalation and exhalation cycles. The lightweight bellows 3 is extremely sensitive to small pressure transients and can even be employed to monitor respiration rates of sleeping infants or the like.

The bellows 3 forms an easily removable and disposable portion of a spirometer or respiration monitoring system and the frame structure 2 can be preserved for multipatient use merely by removing the bellows 3, breathing tube 34 and elbow 35 and inserting replacement parts therefor. Low cost construction, as described below, permits the bellows 3 to be economically disposed and replaced with another.

Manufacturing the expansible and retractible bellows is relatively simple and is accomplished by expanding the helical structure 13 along a longitudinal axis thereof to a desired length in the order of twice the desired operating length. The sheath 22 of thin, fluid-impervious film 23 is extended over the helical structure 13 and end members 27 and 28 applied to opposite ends of the helical structure 13 in a manner to hold the ends of the sheath 22, as by a suitable adhesive. The end members 27 and 28 may be joined to the helical structure 13 at various times in the manufacturing process and may even be joined therewith after completion of the heat shrinking process described below. The assembly is retained in such configuration by suitable means and placed in a heat chamber (not shown). Heat is applied to the film 23 and the film shrunk into engagement with the coils or turns 14. The shrinking shapes the sheath 22 to embrace the helix coils or turns 14 with portions of the upper and lower surfaces 16 and 17 and the outer edge 18 of individual coils or turns 14 with an engagement that prevents relative movement of the contacting portions.

The expanded helical structure 13 is relaxed at a rate in accordance with the rate of shrink of the film 23 whereby the film 23 extends inwardly and radially in folds between the coils or turns 14 and forms a plurality of convolutions 25 extending the length of the helical structure 13. A passage 4 for communicating fluid pressures to the interior of the bellows 3 is provided, in the illustrated example, with the end member 27.

Should it be desired that the bellows 3 have a memory establishing an expanded position less than the desired operating length of the bellows 3 as set forth above, a second series of steps can be added to the above procedure. Relaxation of the helical structure 13 while heat shrinking the film 23 thereon is stopped at a length less than the desired operating length of the helical structure 13. Heat shrinking is continued whereby the film extends inwardly and radially in folds between the coils or turns 14 to more snugly embrace the contacting portions of the coils or turns 14 and set a memory in the convolutions 25 which establishes an intermediate expanded position less than the normally full operating length of the bellows 3. Thereafter, the helical structure 13 is relaxed a second time at a rate in accordance with the rate of shrink of the film to complete the application of the film 23 to the helical structure 13.

It is to be understood that while one form of this invention has been illustrated and described, it is not to be limited to the specific forms or arrangement of parts herein described and shown except insofar as such limitations are included in the following claims.

What is claimed and desired to secure by Letters Patent is:

1. A spirometer comprising:
 (a) an upright, hollow frame structure having opposite end portions;

(b) an expansible and contractible bellows responsive to exhalation and inhalation and including;
  (1) a hollow, resilient helical structure having opposite ends and with a plurality of coils respectively having relatively broad upper and lower surfaces and relatively thin outer edges;
  (2) opposite closed end members connected to the opposite ends of said helical structure, one of said closed end members being connected to one of said end portions for affixing said bellows to said frame structure;
  (3) a sheath of thin, fluid-impervious film extending the length of an expanded said helical structure and situated generally externally thereof, said sheath protruding inwardly and radially between said coils toward a longitudinal axis of said helical structure, thereby forming convolutions of said film embracing said coils only along portions of said upper and lower surfaces and outer edges with a gripping engagement tending to prevent movement of said helical structure relative to said sheath, said sheath joining said opposite closed end members and defining an impervious outer wall structure for said bellows; and
(c) a passage means connected to said one of said closed end members and communicating with an interior of said bellows for transmitting inhalation and exhalation pressures thereto.

2. The spirometer set forth in claim 1 wherein:
(a) said longitudinal axis is substantially vertical;
(b) the opposite end portions of the frame structure are upper and lower members;
(c) said one of the closed end members of the bellows is connected to the lower member of the frame end portions; and
(d) elongate guide members extend between the upper and lower members of the frame structure and define a path for expansive and contractive movement of the bellows.

3. The spirometer set forth in claim 1 wherein:
(a) said longitudinal axis is substantially vertical;
(b) the opposite end portions of the frame structure are upper and lower members; and
(c) said one of the closed end members of the bellows is suspended from the upper member of the frame end portions.

4. The spirometer set forth in claim 1 wherein:
(a) said opposite closed end members include relatively rigid plate members in fluid-tight relation with said sheath.

5. The spirometer set forth in claim 1 including:
(a) volume indicating means extending between said opposite end portions for determining an amount of exhalation and inhalation.

6. A bellows comprising:
(a) a hollow, resilient, expansible and contractible helical structure having opposite ends and with a plurality of coils respectively having relatively broad upper and lower surfaces and relatively thin outer edges;
(b) opposite closed end members connected to the opposite ends of said helical structure;
(c) a sheath of thin, fluid-impervious film extending the length of an expanded said helical structure and situated generally externally thereof, said sheath protruding inwardly and radially between said coils toward a longitudinal axis of said helical structure, thereby forming convolutions of said film embracing said coils only along portions of said upper and lower surfaces and outer edges with a gripping engagement tending to prevent movement of said helical structure relative to said sheath, said sheath joining said closed end members and defining an impervious outer wall structure for said bellows; and
(d) passage means extending into said bellows for communicating fluid pressures thereto.

7. The bellows set forth in claim 6 wherein:
(a) said helical structure has a resilient memory urging said coils toward a contracted position whereby said bellows tends to automatically contract.

8. The bellows set forth in claim 6 wherein:
(a) said helical structure has a resilient memory urging said coils toward an expanded position whereby said bellows tends to automatically expand.

9. A method of making an expansible and contractible bellows comprising the steps of:
(a) providing a hollow, resilient helical structure with a plurality of coils respectively having relatively broad upper and lower surfaces and relatively thin outer edge portions;
(b) expanding said helical structure along a longitudinal axis thereof a desired length;
(c) extending a sheath of thin, fluid-impervious film over the length of the expanded helical structure;
(d) enclosing opposite ends of said helical structure;
(e) heat-shrinking said film inwardly and radially between said coils toward the longitudinal axis of said helical structure forming convolutions of said film embracing portions of said upper and lower surfaces and said outer edges with an engagement retaining said helical structure therein and tending to prevent movement of said helical structure relative to said sheath;
(f) relaxing said helical structure at a rate in accordance with a rate of shrink of said film;
(g) shrinking continuously said film inwardly and radially between said coils;
(h) providing a passage communicating with an interior of said bellows.

10. The method of making a bellows set forth in claim 9 including:
(a) stopping relaxation of said helical structure at a length less than the desired expanded length thereof;
(b) heat-shrinking said film at said length less than the desired expanded length and further forming convolutions in said film extending inwardly and radially between said coils for setting a memory in said convolutions and establishing a second expanded position less than the desired expanded length of said helical structure for low pressure responsiveness of said bellows; and
(c) relaxing said helical structure a second time at a rate in accordance with the rate of shrink of said film.

* * * * *